United States Patent [19]
Stephens

[11] 3,948,104
[45] *Apr. 6, 1976

[54] AUTOMATIC ROTARY SAMPLE INJECTION VALVE

[75] Inventor: Thomas M. Stephens, Menlo Park, Calif.

[73] Assignee: Envirotech Corporation, Menlo Park, Calif.

[ * ] Notice: The portion of the term of this patent subsequent to Feb. 11, 1992, has been disclaimed.

[22] Filed: Oct. 4, 1974

[21] Appl. No.: 511,975

Related U.S. Application Data

[63] Continuation of Ser. No. 443,873, Feb. 19, 1974, Pat. No. 3,864,978.

[52] U.S. Cl. ........................................... 73/422 GC
[51] Int. Cl.² ........................................... G01N 1/10
[58] Field of Search .......... 73/422 GC, 23.1, 61.1 R

[56] References Cited
UNITED STATES PATENTS

| | | | |
|---|---|---|---|
| 3,071,005 | 1/1963 | Skidmore | 73/422 GC |
| 3,824,859 | 7/1974 | Harris et al. | 73/422 GC |
| 3,864,978 | 2/1975 | Stephens | 73/422 GC |

Primary Examiner—S. Clement Swisher
Attorney, Agent, or Firm—Robert E. Krebs; Thomas S. MacDonald

[57] ABSTRACT

A sampling valve includes upper and lower flat-faced body sections that are mounted facing one another for rotation about a generally centrally disposed shaft with a thin seal member interposed between the sections. A reciprocative device selectively rotates the upper body section relative to the lower section through a pre-selected angle about the shaft. A passage is formed from the lower body section to the upper section so that liquid continuously flows through the valve. At one portion of the valve, the passage is in communication with a bore of a sample-taking piston assembly which is arranged on the upper body section. The piston is driven upward to draw a liquid sample from the flowing liquid in the passage and then the upper body section is rotated and the sampling piston is driven downward to eject the sample into a pyrolysis furnace or the like.

5 Claims, 5 Drawing Figures

3,948,104

AUTOMATIC ROTARY SAMPLE INJECTION VALVE

BACKGROUND OF THE INVENTION

This is a continuation of my earlier co-pending U.S. patent application Ser. No. 443,873 filed Feb. 19, 1974 now U.S. Pat. No. 3,864,978.

FIELD OF THE INVENTION

This invention relates generally to a device for automatically procuring liquid samples of a predetermined volume from a continuously flowing stream.

STATE OF THE ART

Accurate sampling is a critical step in the quantitative chemical analysis of liquids. In repetitive or continuous systems, both the volume of sample introduced to the analysis equipment and the manner of sample introduction should be highly reproducable. One presently employed technique of sample introduction is syringe injection through a septum seal. A somewhat different technique is taught in United States patent 3,647,385 wherein sample boats are loaded individually to carry measured amounts of sample into analysis equipment of the pyrolytic type. To take samples from a continuously flowing liquid, it has been suggested to utilize either so-called slide valves or four-way valves. However, both types sometimes fail to deliver uniform volumes of sample and, generally speaking, are better suited for gas samples than for liquids.

OBJECTS OF THE INVENTION

A primary object of the present invention is to provide an automatic sampling device for repetitively introducing a constant volume liquid sample into chemical analysis equipment. A more specific object of the invention is to provide such a device for automatically introducing a liquid sample into quantitative analysis equipment.

BRIEF DESCRIPTION OF THE DRAWINGS

Further objects and advantages of the present invention may be readily ascertained from the following description and appended illustrations which are offered by way of illustration only and not in limitation of the invention, the scope of which is defined by the appended claims and equivalents to the structure, material and steps recited therein. In the drawings:

DETAILED DESCRIPTION OF THE PREFERRED EMBODIMENT

Figure 1:
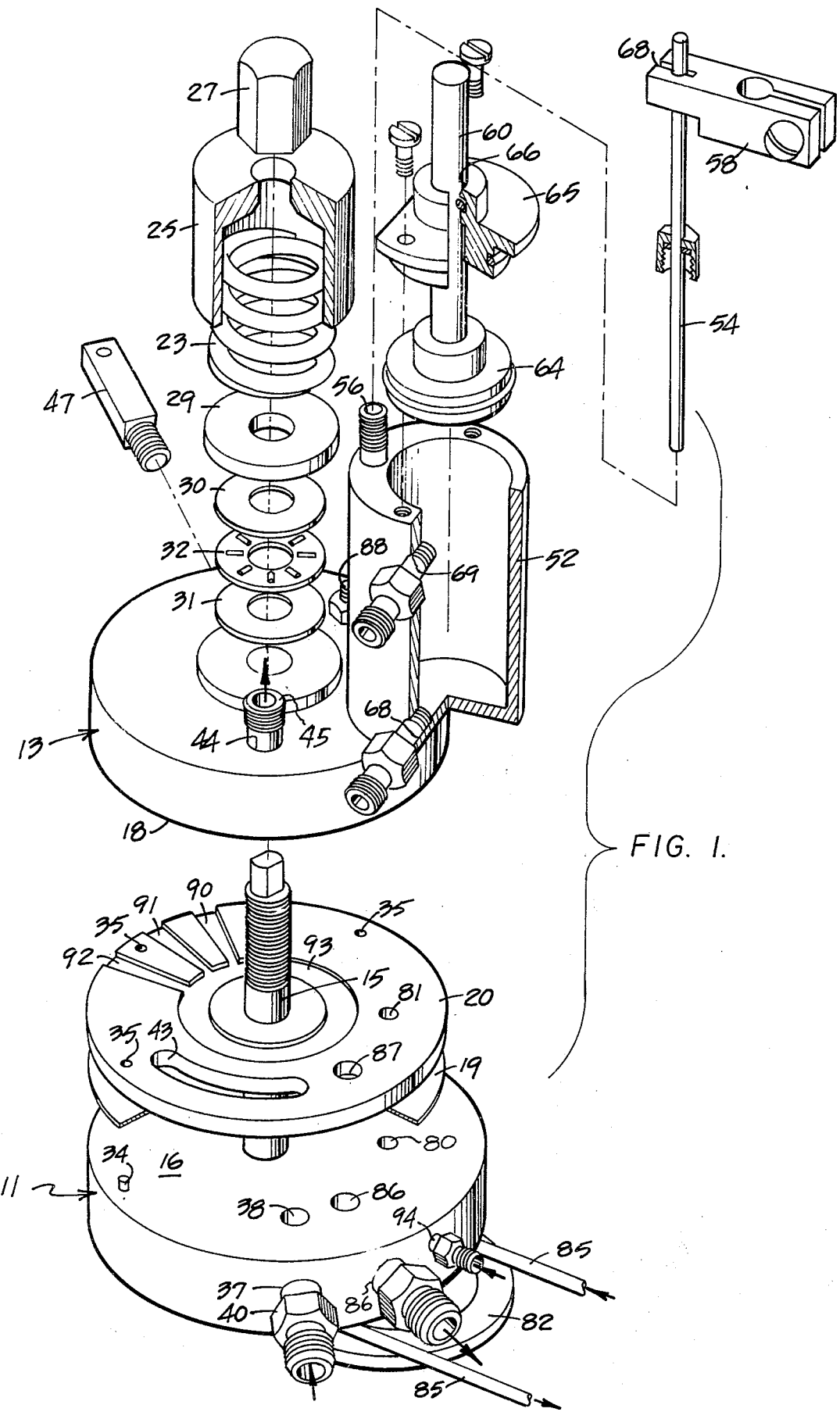
FIG. 1 is an exploded pictorial view, partially cut-away, of a sampling valve according to the present invention.
Figure 2:
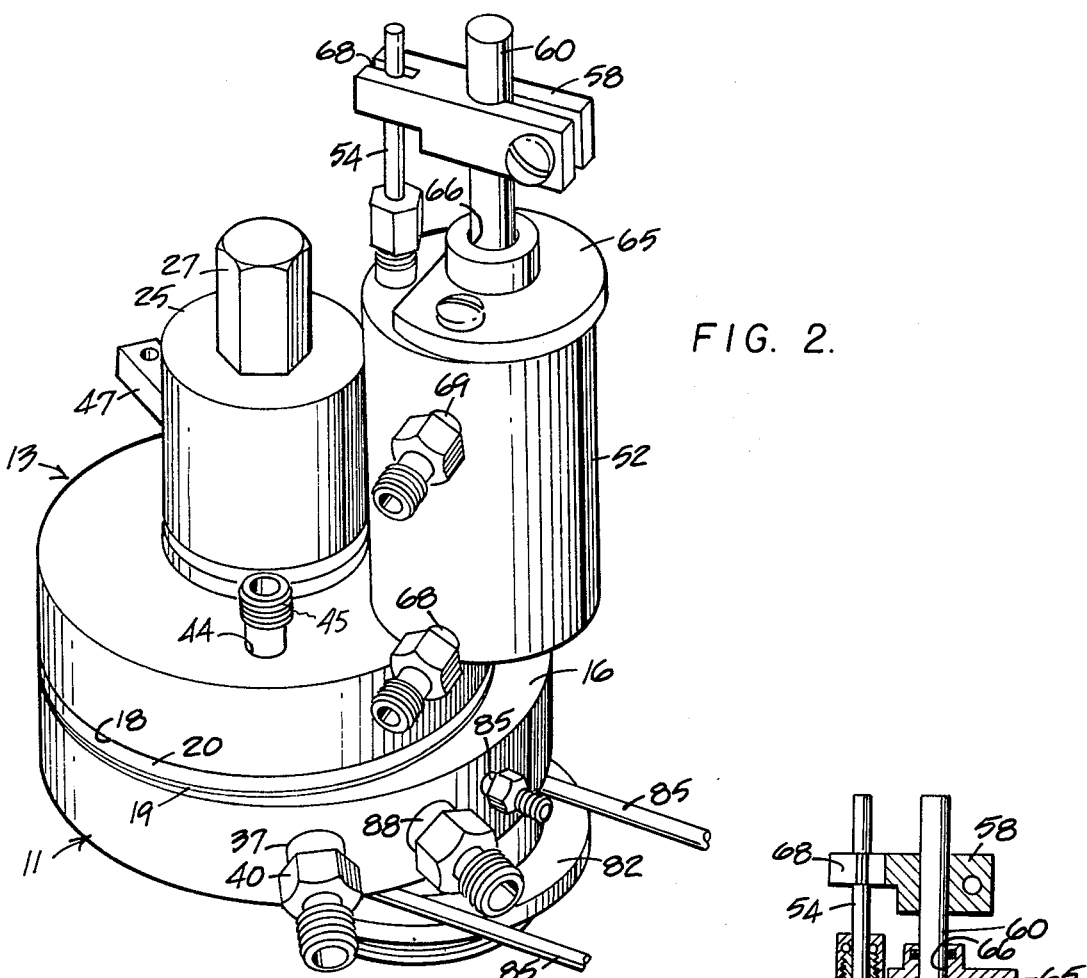
FIG. 2 is a pictorial view of the device of FIG. 1 in assembled condition.

The fluid sampling device or valve shown in FIGS. 1–5 has two body sections 11 and 13 having opposed flat faces 16 and 18 that are constructed and arranged for rotation in parallelism generally concentrically about a shaft 15. The valve assemblage further includes a pair of thin circular seal members 19 and 20 which are sandwiched between the opposed faces of the two body sections concentrically about the shaft 15.

Both body sections are slidable on the shaft 15 and are forced together by a coil spring 23 which encircles the shaft 15 within a sleeve 25 retained by a nut 27. Preferably, flat washers 29–31 and a roller-bearing washer 32 are disposed around the shaft 15 between the spring 23 and the upper body section 13 to minimize friction when the body sections 11 and 13 are rotated relative to one another. The lower end of the shaft 15 is secured by a nut 33 (FIG. 3) whose contact surface is beveled so that the nut acts somewhat like a universal joint to allow slight pivotal freedom of the lower body section 11 relative to the shaft to maintain a sealing relationship between the body sections while accomodating slight misalignment of parts.

The aforementioned circular seal 20 is preferably fabricated from Teflon or a similar material to provide a liquid-tight seal while, at the same time, minimizing friction. The seal 19 is optional in most applications, but is especially useful when salt water samples are taken, in which case it is preferably fabricated from silicon rubber. Both seals 19 and 20 are stationarily located on the lower body section 11 by stub posts 34 that extend into associated holes 35 formed in the seals.

In the lower body section 11, a liquid inlet port 37 is formed in communication with a port 38 that opens into the face 16 at a certain radial distance from the shaft 15. A connector 40 is fitted into the port 37 for coupling to a conduit which carries liquid into the valve. Directly above the port 38, an aperture 41 is formed in the seal 19 and above that aperture, an elongated arc-shaped slot 43 is formed in the seal member 20. The slot 43 extends about seventy-five degrees in a clockwise circumferential direction from its end above the inlet port 38. Above the midline of the arcuate slot 43, a liquid outlet port 44 is formed through the upper body section 13 and a conduit 45 is fitted thereinto to carry liquid from the valve.

Figure 4:
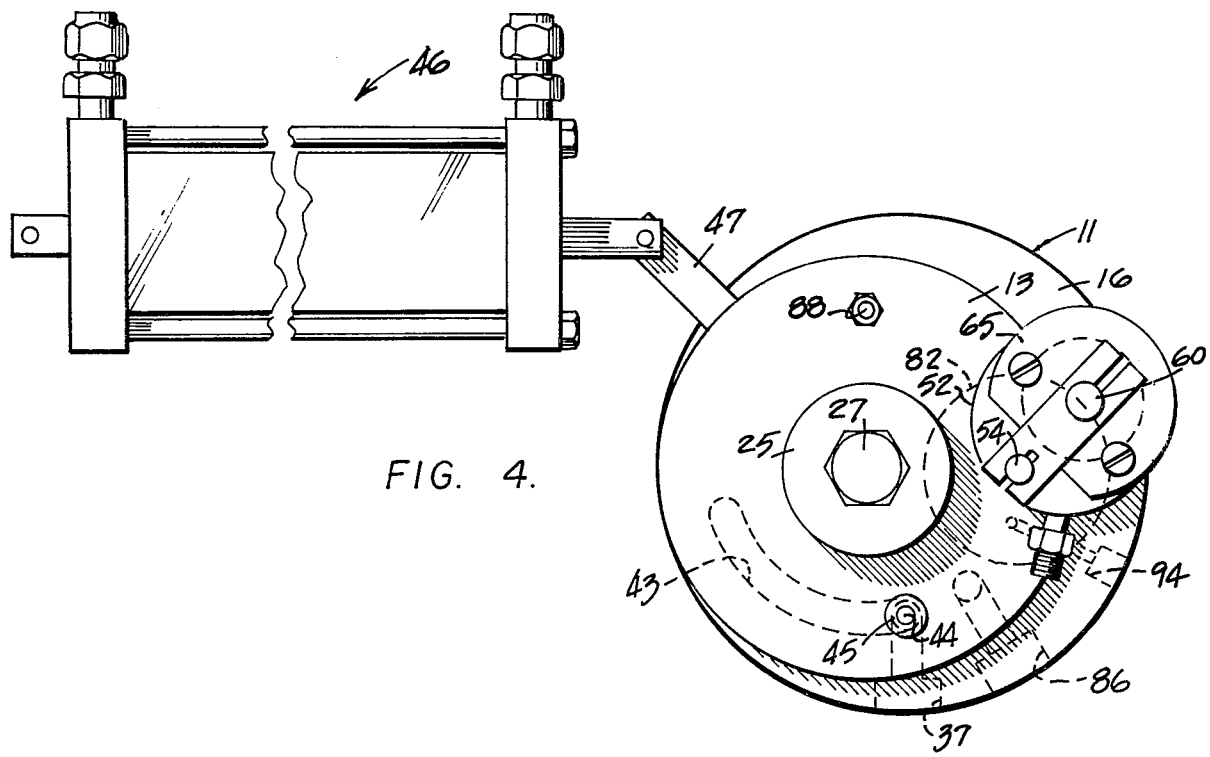
FIG. 4 is a top view of the device of the preceding figures showing some of the hidden parts thereof in dashed lines and with optional equipment connected thereto.
Figure 5:
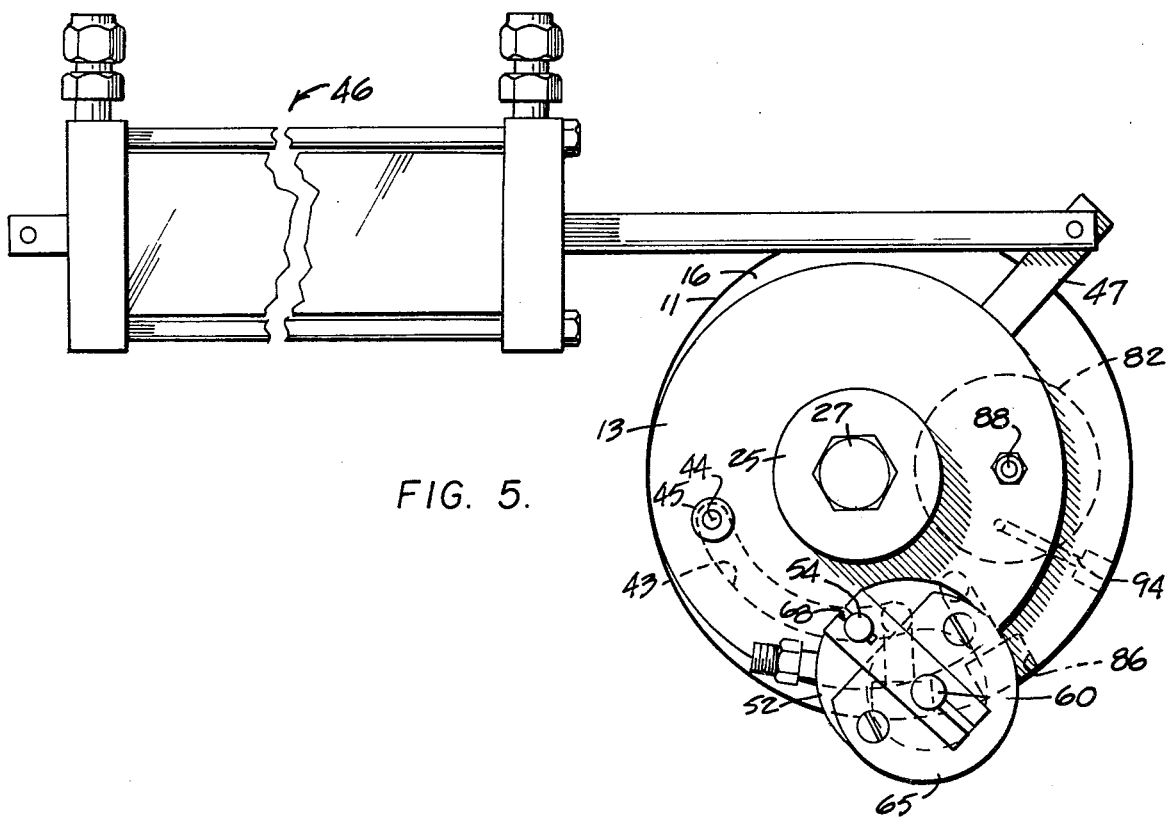
FIG. 5 is a top view similar to FIG. 4 except that a portion of the device is shown in a rotated position.

FIGS. 4 and 5 show one embodiment of means for rotating the body sections relative to each other to transfer a sample from the "up-take" location to the "eject" location. In the illustrated arrangement, a hydraulically or pneumatically actuated piston assembly 46 is pivotally attached at one end to an arm 47 fixed to the upper body section 13 so that relative rotation of the two body sections is effectuated by extension and contraction of the piston assembly 46. FIG. 4 shows the valve in the sample eject orientation and FIG. 5 shows the upper body section rotated about 75° clockwise by extension of the piston assembly to the sample up-take position. It should be noted that the terminal points of the rotation are determined such that port 44 is always in fluid-flow communication with the slot 43.

Referring again to FIGS. 1–3, a cylindrical member 52 is fixed to the upper body section 13 and a rod 54 is disposed for sliding reciprocation in a bore 56 that extends lengthwise through the sidewall of cylinder 52 and thence through the upper body section 13 into communication with the face 18 of that section at the same radial distance from the shaft 15 as the midline of the arcuate slot 43. In the sample up-take position (FIG. 5), the valve body sections 11 and 13 are disposed with the bore 56 directly above the slot 43 so that the lower or distal end of the rod 54 serves as a piston for drawing a sample volume of liquid from the slot 43 into the bore 56.

The upper end of the rod 54 is adjustably connected by a link 58 to the stem 60 of an annular piston 64 which is slidably disposed within the cylinder 52. The upper end of the cylinder is closed by a cap member 65 having an aperture 66 formed therethrough to accomodate the piston stem. The piston 64 is movable up and down in the cylinder 52 by the selective introduction of pressurized gas through the ports 68 and 69 at the respective ends of the cylinder. The aforementioned link 58 preferably includes a slot 68 which mates with a groove in the upper end of the rod 54 to permit slight pivotal movement at the connection. The other end of the link 58 is adapted for adjustable positioning on the piston stem 60 so that the bottom end of rod 54 can be positioned exactly even with the surface of face 18 when the piston 64 is bottomed in the cylinder 52.

With the illustrated assemblage, there are two ways to change the volume of sample drawn by the rod 54. First, the diameter of the rod 54 and bore 56 can be altered. Secondly, a washer can be placed on top of piston 64 to limit the piston travel and, thus, the effective stroke of the rod 54. In practice, the sample volume is typically about 250 micro-liters but can be accurately set as low as 100 micro-liters or as high as 500 micro-liters.

Figure 3:
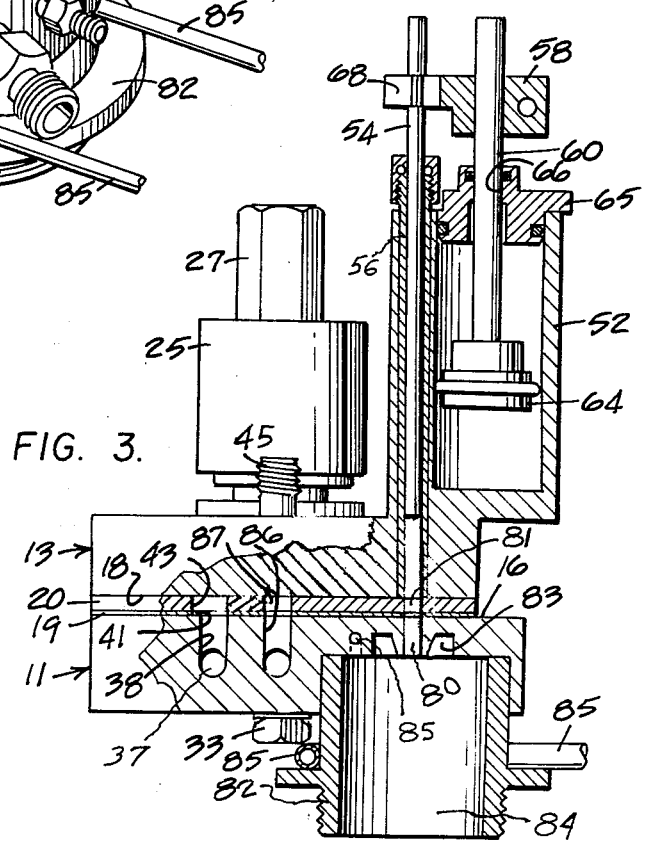
FIG. 3 is a side view, partially cut-away, of the device of preceding figures.

As best shown in FIG. 3, a port 80 is formed through the lower body section 11 in communication with the face 16 thereof at exactly the same radial distance from the shaft 15 as the bore 56. Above the port 80, a passage 81 is formed through the seal members 19 and 20 so that liquid ejected by the sampling rod 54 from the bore 56 can directly enter the port 80. A threaded coupling 82 for connection to a pyrolysis tube or the like is fitted into the base of body section 11 in a cavity 84 surrounding the discharge end of the port 80. A groove 83 preferably is also formed immediately around the discharge end of the outlet port 80 to give the exterior of the port a conical shape; such a shape has been found to minimize surface tension effects as samples drop from the port 80. In the upper body section 13, there is formed a port 88 at a location such that it is in communication with outlet port 80 via the passage 81 when the valve is in the sample up-take position. The port 88 can be used to feed carrier gas into the outlet port while sample is being drawn; it can also be used to inject samples by hand when a system is being calibrated.

In most applications, it is desirable to maintain the port 80 and the coupling 82 at a constant low temperature. To accomplish that, the illustrated device includes a heat exchanging tube 85 that fixedly surrounds the outlet coupling 82 to carry fluid to cool the coupling. Without cooling means, heat from a pyrolysis tube is apt to destroy the pyrolysis tube's seals and gaskets where the tube is secured to the coupling 82.

Referring again to FIG. 1, a drainage port 86 is formed in communication with the face 16 of the lower body section 11 at a location between the inlet port 38 and the sample eject port 80 to drain liquid leakage from the valve before such leakage reaches the sample eject port 80 where it would cause quantitative errors in the subsequent chemical analysis. Directly above the drainage port 86, a passage 87 is formed through the seal members 19 and 20 to intercept liquid leakage along the upper faces of the seal members. To further prevent liquid leakage from reaching the sample eject port 80, a plurality of radially-extending drainage grooves 90, 91 and 92 are formed in the upper face of the seal member 20 in communication with a circular groove 93 surrounding shaft 15 to carry liquid leakage to discharge at the side of the valve.

A carrier gas port 94 is formed through the lower body section 11 in flow communication with the cavity 84 that surrounds the outlet end of the sample eject port 80. Carrier gas, such as oxygen or air, is injected through the gas port 94 to sweep the liquid samples through the coupling into subsequent analysis equipment.

In operation, a stream of liquid is continuously introduced to the valve at the inlet port 37. Such liquid continuously flows through the valve via the port 38 in the face 16 of the lower body section, the aperture 41 in the circular seal 19, the slot 43 in the circular seal 20, and the outlet port 44 in the upper body section 13. The continuous upward flow of liquid through the valve is effective to prevent gaseous bubbles from being trapped within the valve; if such bubbles were trapped, there is the likelihood that they would be drawn in with the samples by the rod 54, thereby making the sample volumes erratic. The continuous liquid flow and the relatively large diameter flow paths in the valve also readily permit the passage of most particles (up to 2.5 mm) which may be present in the liquid.

To procure a single sample from the stream, the upper body section 13 is rotated from the FIG. 4 position to the position shown in FIG. 5 where the rod 54 is in the fully upward position and is directly above the slot 43. At that time, the lower end of the bore 56 usually contains a quantity of carrier gas which entered the bore when the valve was in the FIG. 4 position. To discharge the trapped gas, the rod 54 is driven downward by operation of the piston 64, thereby causing the gas to enter the slot 43 as a large bubble. This carrier gas bubble will agglomerate any smaller bubbles which may be in the slot 43 because of sample degasification. The agglomerated bubbles then are entrained in the liquid flowing through the valve and pass upward to discharge through outlet 44. After a short pause to allow time for escape of the gas bubbles, the rod 54 is driven upward by actuation of the piston 64 and causes liquid to be drawn into the bore 56. In usual practice, the rod is then forced downward once again to wash the bore 56 with the fresh sample and finally is retracted upward a second time to take the actual sample. Once the final sample is drawn into the bore 56, the upper body section 13 is rotated by the piston assembly 46 until the bore 56 is directly above the outlet port 80 (FIG. 4) and the rod 54 is then driven downward to eject the sample, which then drops into a pyrolysis tube or the like which is connected to the coupling 82. Throughout the entire operating cycle, carrier gas is continuously passed through the port 94 to sweep sample residue out of the cavity 84 and into the analysis equipment. Following sample ejection, the rod 54 is returned to its upward position and then the upper valve body 13 is rotated to bring bore 56 back to its initial position above the arcuate slot 43.

I claim:

1. A device for procuring samples of a predetermined volume from a continuously flowing liquid stream comprising:
    a. a valve body inclusive of upper and lower sections which are constructed and arranged to present flat faces each to the other;

b. at least one seal member interposed between said parallel faces of said sections;

c. means connected to said sections to rotate one section relative to the other through a preselected angle from a first position to a second position while maintaining parallelism between said faces;

d. a liquid inlet port formed through said lower section in fluid-flow communication with the flat face thereof and a liquid outlet port formed through said upper section in communication with the flat face thereof;

e. a slot formed through said at least one seal member connecting said inlet and outlet ports in continuous fluid-flow communication with each other between said first and second positions;

f. piston means arranged to travel in a bore formed in said upper section, which bore is located for communication with said slot at said first position;

g. actuating means to actuate said piston to travel in said bore to effectuate the drawing into said bore of a liquid sample from said slot at said first position of said body sections; and h. a sample eject port formed through said lower body section and through said at least one seal member at a location spaced from said inlet port and said slot for receiving a liquid sample of predetermined volume released from said bore by action of said actuating means at said second position of said body sections.

2. A device according to claim 1 further including a drainage port formed through said face of said lower section at a position between said eject port and said outlet port.

3. A device according to claim 1 further including a carrier gas port formed in communication with said eject port for carrying gas to sweep sample from said valve.

4. A device according to claim 1 wherein there are two seal members interposed between said parallel faces of said sections.

5. A device according to claim 1 wherein sample is drawn into said bore by the upward travel of said piston means and sample is ejected from said bore by the downward travel of said piston.

* * * * *